US012767943B2

(12) United States Patent
Tajima

(10) Patent No.: US 12,767,943 B2
(45) Date of Patent: Oct. 20, 2026

(54) SPECIMEN PROCESSING APPARATUS

(71) Applicant: UNIVERSAL BIO RESEARCH CO., LTD., Chiba (JP)

(72) Inventor: Hideji Tajima, Chiba (JP)

(73) Assignee: UNIVERSAL BIO RESEARCH CO., LTD., Chiba (JP)

( * ) Notice: Subject to any disclaimer, the term of this patent is extended or adjusted under 35 U.S.C. 154(b) by 441 days.

(21) Appl. No.: 18/561,218

(22) PCT Filed: May 27, 2022

(86) PCT No.: PCT/JP2022/021683

§ 371 (c)(1),
(2) Date: Nov. 15, 2023

(87) PCT Pub. No.: WO2022/255236

PCT Pub. Date: Dec. 8, 2022

(65) Prior Publication Data

US 2024/0254471 A1 Aug. 1, 2024

(30) Foreign Application Priority Data

May 31, 2021 (JP) ................................ 2021-091568

(51) Int. Cl.
*C12N 15/10* (2006.01)
*G01N 35/10* (2006.01)

(52) U.S. Cl.
CPC ..... *C12N 15/1003* (2013.01); *G01N 35/1081* (2013.01)

(58) Field of Classification Search
CPC ........... C12N 15/1003; G01N 35/1081; G01N 35/04; G01N 35/1074; G01N 2035/0413; C12Q 1/6806
See application file for complete search history.

(56) References Cited

U.S. PATENT DOCUMENTS

2006/0133965 A1* 6/2006 Tajima ............... G01N 35/1065 422/63
2010/0137574 A1 6/2010 Bachmann et al.
2022/0017890 A1 1/2022 Lee

FOREIGN PATENT DOCUMENTS

JP 2010-127941 A 6/2010
JP 2015-139398 A 8/2015
(Continued)

OTHER PUBLICATIONS

International Search Report and Written Opinion received in PCT/JP2022/021683 mailed Aug. 9, 2022.
(Continued)

*Primary Examiner* — Michael L Hobbs
(74) *Attorney, Agent, or Firm* — Meunier Carlin & Curfman LLC

(57) ABSTRACT

A specimen processing apparatus 1000 comprising: a plurality of container holders 510 holding, in one row, a plurality of second nucleic acid containers housing the nucleic acids; a pitch conversion mechanism 500 converting a pitch of the plurality of container holders between a smaller pitch and a larger pitch; a plurality of treatment lanes extracting the plurality of nucleic acid from a plurality of specimens in parallel; a first nozzle unit 200 including a plurality of first nozzles 210 disposed in one row at the greater pitch and moving over the plurality of treatment lanes; a PCR plate 128 having a plurality of wells disposed in one row at the smaller pitch; a second nozzle unit 300 including a plurality of second nozzles 310 disposed in one row at the smaller pitch and moving between a location above the plurality of container holders having the smaller pitch and a location above the PCR plate 128; and a control unit controlling operation of respective parts.

15 Claims, 9 Drawing Sheets

(56) References Cited

FOREIGN PATENT DOCUMENTS

| | | | | | |
|---|---|---|---|---|---|
| JP | 2019-113416 | A | | 7/2019 | |
| WO | 2002/081087 | A1 | | 10/2002 | |
| WO | WO-2020093824 | A1 | * | 5/2020 | ......... G01N 35/1083 |

OTHER PUBLICATIONS

Extended European Search Report received in PCT/JP2022/021683 mailed May 8, 2025.

* cited by examiner

SPECIMEN PROCESSING APPARATUS

CROSS-REFERENCE TO RELATED APPLICATIONS

This application is a U.S. National Stage application filed under 35 U.S.C. § 371 of PCT/JP2022/021683 filed May 27, 2022, which claims the benefit of priority to Japanese Application No. 2021-091568 filed May 31, 2021.

TECHNICAL FIELD

The present invention relates to a specimen processing apparatus that concurrently extracts nucleic acids from a plurality of specimens, and more specifically relates to a specimen processing apparatus in which the pitch of a plurality of holders can be converted, the plurality of holders holding specimens and/or extracted nucleic acids.

BACKGROUND ART

For detection of pathogens, such as viruses, the PCR method is used, which has become widespread with the development of genetic engineering, and which makes use of polymerase chain reaction (PCR). A specimen (saliva, nasopharyngeal swab fluid, or the like) containing a pathogen is taken with a commercially available sampling kit, a nucleic acid (DNA or RNA) is extracted from the specimen, the nucleic acid is amplified by the PCR method, and the pathogen is then detected based on the amplified nucleic acid. The world has been exposed to the new coronavirus (COVID-19) pandemic since the end of 2019. The PCR method has been used for detecting COVID-19.

Although the PCR method is performed mainly by manual handling, manual handling not only has difficulties in continuously performing a large amount of inspection processing, but also has the possibility of erroneous operations or contamination occurring in processing steps. In view of the above, an automated PCR test device that automatically performs the PCR method is proposed. For example, a fully automated sample-to-result PCR system (geneLEAD series) made by Precision System Science Co., Ltd. can be used as the automated PCR test device. This fully automated sample-to-result PCR system can perform, without manual intervention, a PCR test by extracting specimens from specimen containers that house the specimens.

In the case of performing the PCR method without using the automated PCR test device, a plurality of nucleic acids that are manually extracted from a plurality of specimens are dispensed into a plurality of wells of a PCR plate, and the PCR method is performed with the PCR plate housed in a thermal cycler. A 96-well PCR plate is used for the PCR plate, for example. By using the 96-well PCR plate, it is possible to simultaneously amplify nucleic acids extracted from 96 specimens at maximum. Such a PCR and the thermal cycler is described in, for example, Patent Literature 1, International Publication No. WO 2002/081087.

CITATION LIST

Patent Literature

Patent Literature 1: International Publication No. WO 2002/081087

SUMMARY OF INVENTION

Technical Problem

By using the above-described fully automated sample-to-result PCR system, extraction of nucleic acids from a plurality of specimens, amplification of the nucleic acids, and detection of the nucleic acids can be concurrently and continuously performed. However, this fully automated sample-to-result PCR system does not allow use of a conventional PCR plate or a thermal cycler.

In view of the above, it is an object of the present invention to provide a specimen processing apparatus that concurrently extracts nucleic acids from a plurality of specimens, and that collectively moves the extracted nucleic acids to a container, such as a PCR plate.

Solution to Problem

Respective aspects of the present invention have the following configurations.

[Aspect 1]

A specimen processing apparatus that extracts nucleic acids from a plurality of specimens, the specimen processing apparatus including:

- a plurality of container holders configured to hold a plurality of first specimen containers and/or a plurality of first nucleic acid containers in one row along a first direction, the plurality of first specimen containers housing the plurality of specimens along the first direction, the plurality of first nucleic acid containers housing the nucleic acids extracted along the first direction;
- a pitch conversion mechanism configured to convert a pitch of the plurality of container holders along the first direction between a smaller pitch and a larger pitch;
- a plurality of processing lanes extending in a second direction in parallel in order to concurrently extract the nucleic acids from the plurality of specimens;
- a first nozzle unit including a plurality of first nozzles arranged in one row along the first direction at the larger pitch, the first nozzle unit being configured to move over the plurality of processing lanes along the second direction;
- a second container housing unit configured to house a plurality of second specimen containers and/or a plurality of second nucleic acid containers, the plurality of second specimen containers being arranged in one row along the first direction at the smaller pitch, the plurality of second nucleic acid containers being arranged in one row along the first direction at the smaller pitch;
- a second nozzle unit including a plurality of second nozzles arranged in one row along the first direction at the smaller pitch, the second nozzle unit being configured to move between a region above the plurality of container holders set to the smaller pitch and a region above the second container housing unit; and
- a control unit configured to control an operation of the pitch conversion mechanism, an operation of the first nozzle unit, and an operation of the second nozzle unit.

[Aspect 2]

The specimen processing apparatus described in aspect 1, including a main moving mechanism configured to move the first nozzle unit in the second direction.

[Aspect 3]

The specimen processing apparatus described in aspect 1 or 2, wherein the main moving mechanism moves the second nozzle unit in the second direction.

[Aspect 4]

The specimen processing apparatus described in any one of aspects 1 to 3, wherein the main moving mechanism moves the first nozzle unit and the second nozzle unit as an integral body.

[Aspect 5]

The specimen processing apparatus described in any one of aspects 1 to 4, including a sub-moving mechanism configured to move the second nozzle unit in the first direction.

[Aspect 6]

The specimen processing apparatus described in any one of aspects 1 to 5, wherein the second container housing unit that houses the plurality of second nucleic acid containers is a PCR plate having a plurality of wells.

[Aspect 7]

The specimen processing apparatus described in any one of aspects 1 to 6, including a pitch conversion mechanism moving mechanism configured to move the pitch conversion mechanism in the first direction.

[Aspect 8]

The specimen processing apparatus described in any one of aspects 1 to 7, wherein the plurality of container holders, the pitch conversion mechanism, and the plurality of processing lanes are disposed on a first stage.

[Aspect 9]

The specimen processing apparatus described in aspect 8, wherein the first nozzle unit moves over the first stage.

[Aspect 10]

The specimen processing apparatus described in aspect 8 or 9, wherein the first stage is provided with a dispensing tip disposal unit configured to dispose of dispensing tips mounted on the plurality of first nozzles and/or dispensing tips mounted on the plurality of second nozzles.

[Aspect 11]

The specimen processing apparatus described in any one of aspects 1 to 10, wherein the second container housing unit is disposed on a second stage.

[Aspect 12]

The specimen processing apparatus described in aspect 11, including a cooling mechanism configured to cool the second container housing unit.

[Aspect 13]

The specimen processing apparatus described in aspect 11 or 12, wherein the second nozzle unit moves over at least the second stage.

[Aspect 14]

The specimen processing apparatus described in any one of aspects 1 to 13, wherein the plurality of container holders house the plurality of specimen containers at a position closer to the plurality of processing lanes than the plurality of nucleic acid containers in the second direction.

[Aspect 15]

The specimen processing apparatus described in any one of aspects 1 to 14, wherein the pitch conversion mechanism includes a plurality of holder support parts, a link mechanism, a slide piece, and a slide piece drive mechanism, the plurality of holder support parts being configured to support the plurality of container holders such that each of the plurality of container holders is movable in the first direction, the link mechanism being connected to the plurality of holder support parts, the slide piece being configured to cause the link mechanism to slide between the smaller pitch and the larger pitch, the slide piece drive mechanism being configured to drive the slide piece.

Advantageous Effect of Invention

The specimen processing apparatus of the present invention can concurrently extract nucleic acids from a plurality of specimens, and can collectively move the extracted nucleic acids to a container, such as a PCR plate.

DESCRIPTION OF EMBODIMENTS

An embodiment relating to a specimen processing apparatus of the present invention will be described with reference to drawings. In the respective drawings, identical components are given the same reference symbols, and the description of such components will be omitted when appropriate. In the respective drawings, relative sizes and/or arrangement of respective components are accurately illustrated in principle. However, the present invention is not limited to such relative sizes and/or arrangement of the respective components. In the embodiment of the present invention, a specimen is a living-body-related substance, and a body fluid taken from a living body, or any dissolvable tissue may be preferably used. Note that the x direction and the y direction in the embodiment respectively correspond to the first direction and the second direction in Claims.

[Basic Configuration of Specimen Processing Apparatus]

Figure 1:
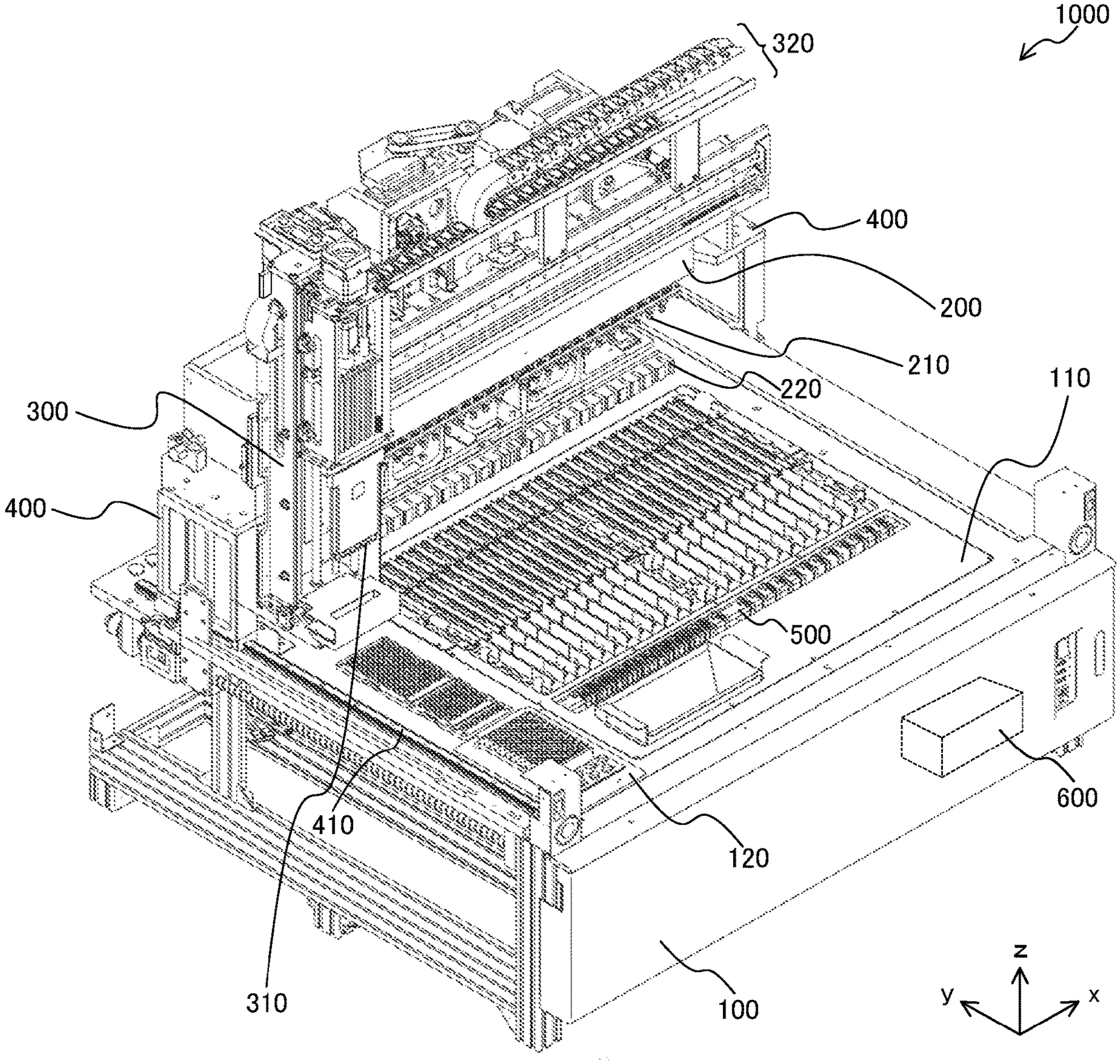
FIG. 1 is a perspective view showing a specimen processing apparatus according to one embodiment of the present invention.

The basic configuration of a specimen processing apparatus 1000 according to an embodiment of the present invention will be described with reference to FIG. 1. As shown in FIG. 1, the specimen processing apparatus 1000 includes a base 100, a first nozzle unit 200, a second nozzle unit 300, a main moving mechanism 400, a pitch conversion mechanism 500, and a control unit (computer) 600. The base 100 supports respective components. The first nozzle unit 200 is provided for performing processing (extraction of nucleic acids or the like) on a plurality of specimens. The second nozzle unit 300 is provided for moving the plurality of specimens and/or a plurality of nucleic acids. The main moving mechanism 400 supports the first nozzle unit 200 and the second nozzle unit 300, and moves the first nozzle unit 200 and the second nozzle unit 300 in the y direction. The control unit 600 controls the operations of the respective components.

[Configuration of Specimen Processing Apparatus as Viewed from Above]

Figure 2:
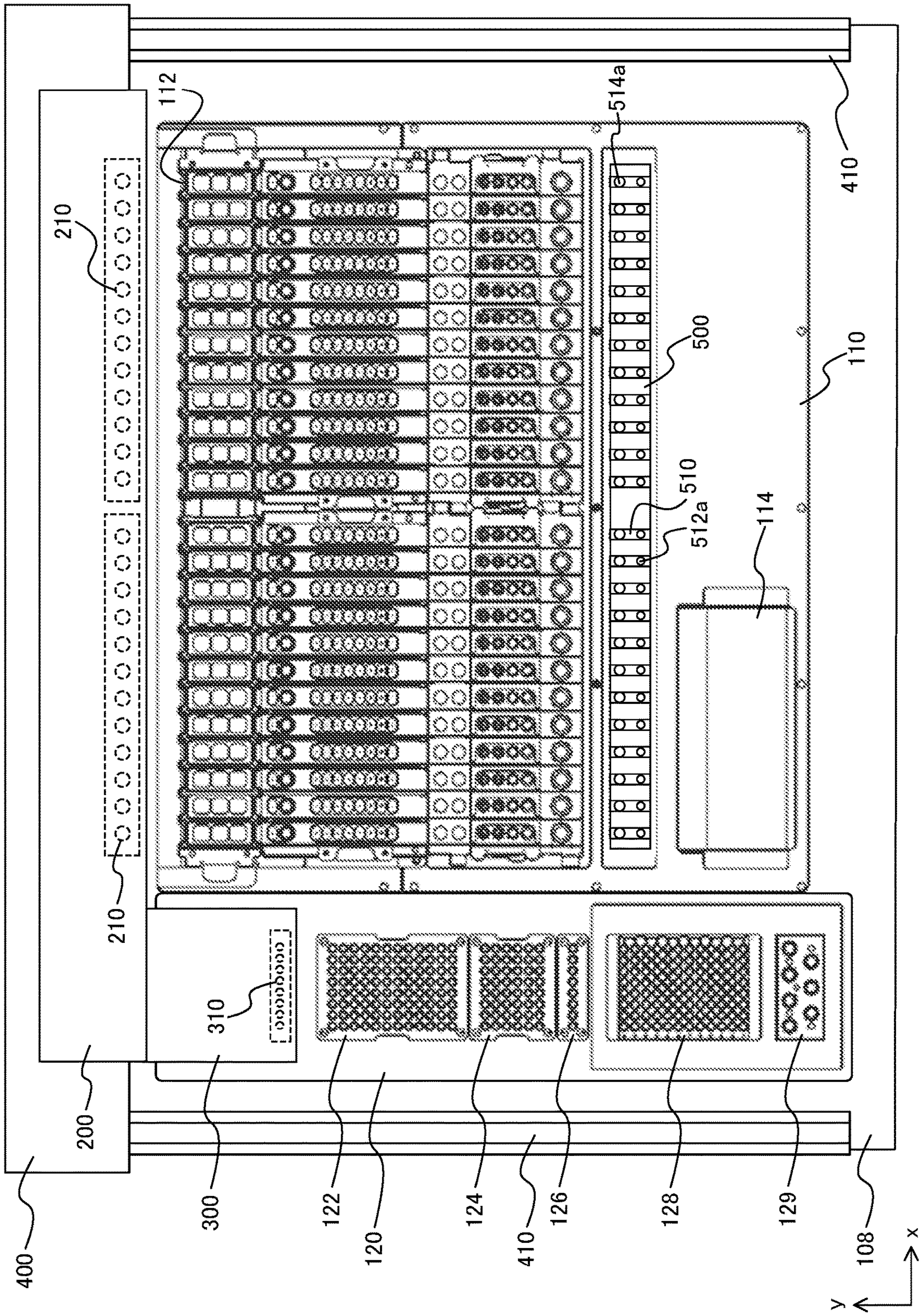
FIG. 2 is a top plan view showing the specimen processing apparatus that includes a pitch conversion mechanism set to a larger pitch.

As shown in FIG. 2, which is a top plan view, an upper surface 108 of the specimen processing apparatus 1000 includes a first stage 110 and a second stage 120. Processing, such as extraction of specimens, is performed on the first stage 110. Instruments, reagent, and the like used for performing processing on specimens are held on the second stage 120. The first stage 110 is provided with a plurality of processing lanes 112 and an opening 114 of a dispensing tip disposal unit. The plurality of processing lanes 112 extend in the y direction in parallel. A plurality of extraction cartridges, a plurality of dispensing tips, piercing tips, and the like are arranged in one row on each processing lane 112. Each extraction cartridge has a plurality of wells arranged in one row.

The pitch conversion mechanism 500 including a plurality of container holders 510 is disposed on one end side of the plurality of processing lanes 112. As will be described later, the pitch conversion mechanism 500 can convert the pitch of the plurality of container holders 510 in the x direction between a larger pitch (22 mm pitch, for example) and a smaller pitch (9 mm pitch, for example). It is sufficient that the larger pitch be relatively larger than the smaller pitch.

Figure 3:
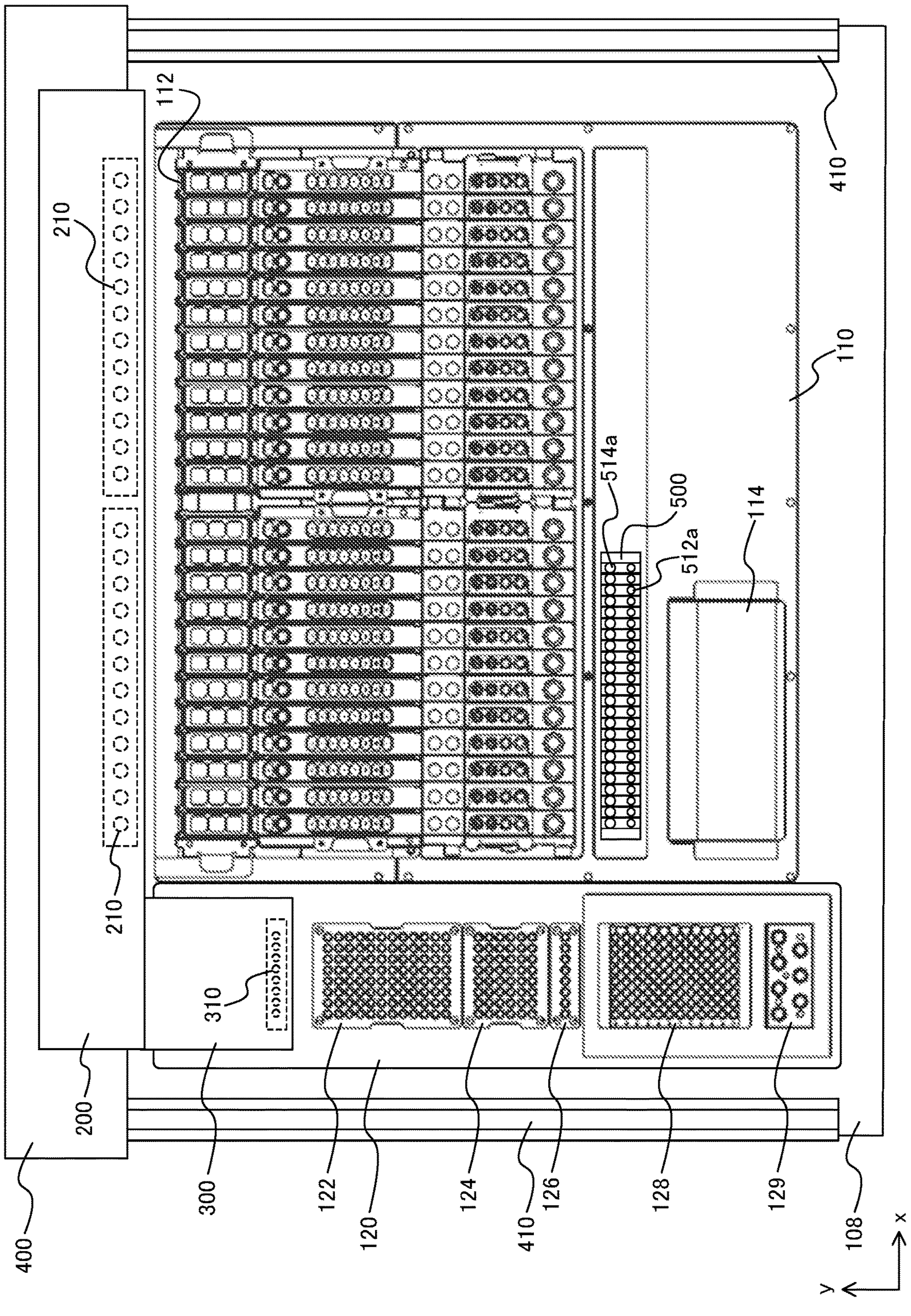
FIG. 3 is a top plan view showing the specimen processing apparatus that includes the pitch conversion mechanism set to a smaller pitch.

In FIG. 2, the pitch conversion mechanism 500 is set to the larger pitch and hence, each container holder 510 and each of the plurality of processing lanes 112 are arranged in one row along the y direction. That is, each container holder 510 is aligned with each of the plurality of processing lanes 112 along the y direction. In FIG. 3, the pitch conversion mechanism 500 is set to the smaller pitch and hence, each container holder 510 is not aligned with each of the plurality of processing lanes 112 in the y direction as a whole.

As shown in FIG. 2 and FIG. 3, the second stage 120 is provided with dispensing tip housing units 122, 124 for the second nozzle unit 300, a specimen container housing unit (second container housing unit) 126, a PCR plate 128 (second container housing unit), and a PCR reagent storage unit 129. The specimen container housing unit 126 is configured to house a plurality of second specimen containers in one row along the x direction. A cooling mechanism is provided below the PCR plate 128 and/or the PCR reagent storage unit 129. It is preferable that the PCR plate 128 have eight wells arranged in each row along the x direction, and have twelve wells (second nucleic acid containers) arranged in each column along the y direction.

As shown in FIG. 2 and FIG. 3, which are top plan views, the main moving mechanism 400 is movable in the y direction along a pair of rails 410 provided on the upper surface 108. The control unit 600 controls the movement of the main moving mechanism 400 by driving a moving motor not shown in the drawing. The first nozzle unit 200 is moved in the y direction over the first stage 110 as an integral body with the main moving mechanism 400. The first nozzle unit 200 includes a plurality of first dispensing nozzles 210 arranged in one row along the x direction. Each first dispensing nozzle 210 is movable over each processing lane 112. The first nozzle unit 200 includes a first dispensing nozzle motor that allows the plurality of first dispensing nozzles 210 to perform suction and discharge. The first nozzle unit 200 includes a magnetic force mechanism 220 (FIG. 1) that exerts a magnetic force on dispensing tips, with the dispensing tips mounted at the lower end portions of the respective first dispensing nozzles 210. The magnetic force mechanism 220 includes a magnetic force mechanism motor that allows the magnetic force mechanism 220 to advance and retract in the y direction. The control unit 600 controls the operations of the respective motors.

The second nozzle unit 300 is integrally formed with the main moving mechanism 400 and/or the first nozzle unit 200. The second nozzle unit 300 is moved in the y direction over the first stage 110 and the second stage 120. The second nozzle unit 300 includes a plurality of second dispensing nozzles 310 arranged in one row along the x direction. The respective second dispensing nozzles 310 are movable over the second stage 120 in the state shown in FIG. 2. The respective second dispensing nozzles 310 are movable over the first stage 110 in the state shown in FIG. 6.

The second nozzle unit 300 includes a second dispensing nozzle motor that allows the plurality of second dispensing nozzles 310 to perform suction and discharge. The control unit 600 controls the operations of the respective motors. The second nozzle unit 300 includes a sub-moving mechanism 320 (FIG. 1) that moves the second nozzle unit 300 in the x direction with respect to the main moving mechanism 400 and/or the first nozzle unit 200. The control unit 600 controls the operation of the sub-moving mechanism 320. The sub-moving mechanism 320 is provided to the main moving mechanism 400.

[Pitch Conversion Mechanism]

Figure 4:
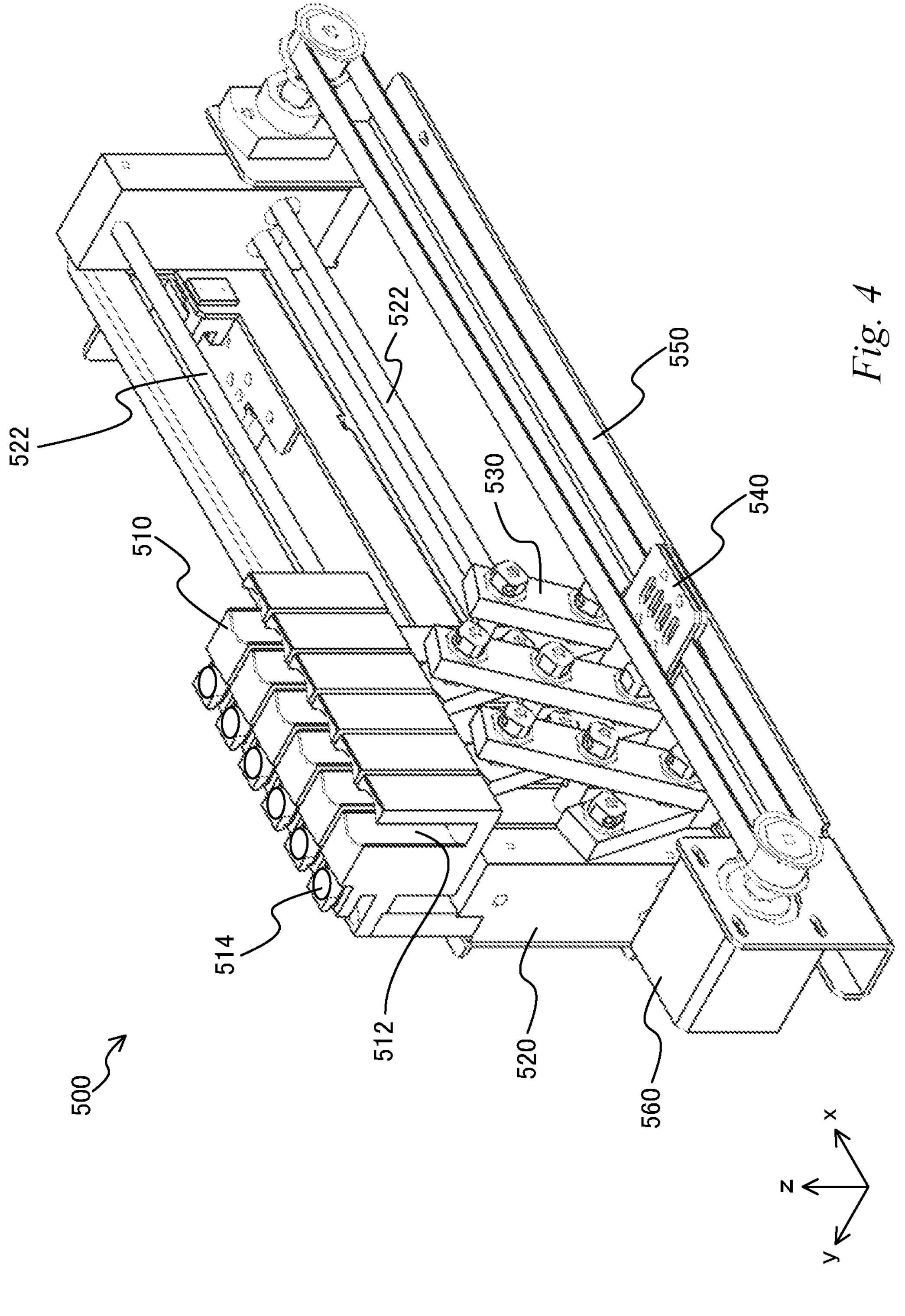
FIG. 4 is a perspective view showing the pitch conversion mechanism set to the smaller pitch.
Figure 5:
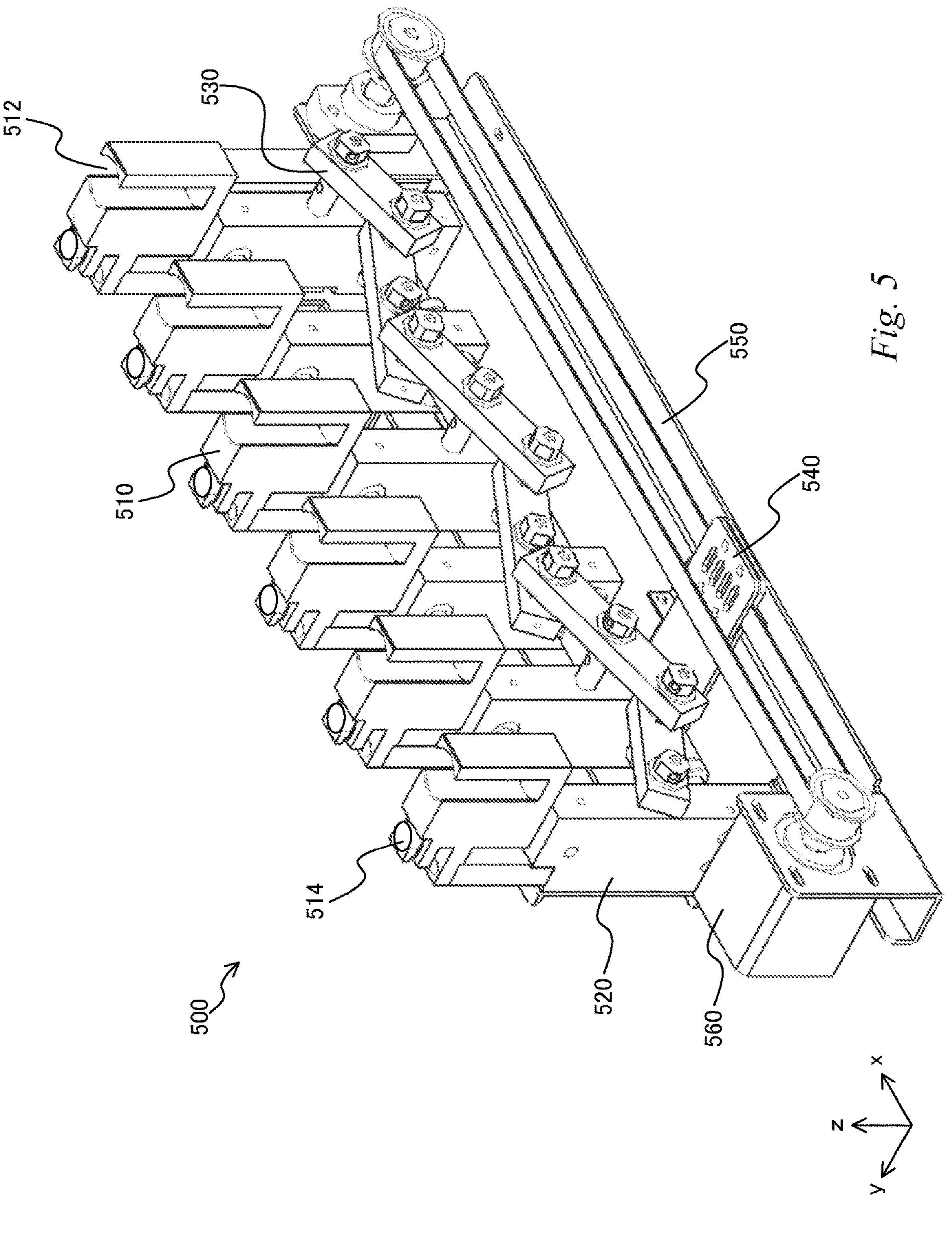
FIG. 5 is a perspective view showing the pitch conversion mechanism set to the larger pitch.

The pitch conversion mechanism 500 will be described with reference to FIG. 4 and FIG. 5. In FIG. 4 and FIG. 5, portions of the pitch conversion mechanism 500 that are repeated in the x direction are illustrated in a partially omitted manner. The pitch conversion mechanism 500 set to a smaller pitch is shown in FIG. 3 and FIG. 4, and the pitch conversion mechanism 500 set to a larger pitch is shown in FIG. 2 and FIG. 5.

As shown in FIG. 4 and FIG. 5, the pitch conversion mechanism 500 includes the plurality of container holders 510, nucleic acid container holding spaces 512, specimen container holding spaces 514, a plurality of holder support parts 520, one or a plurality of guide rod (guide part) 522, a link mechanism 530, a slide piece 540, a drive belt 550, and a drive belt motor 560. The nucleic acid container holding space 512 is provided to each of the plurality of container holders 510. The specimen container holding space 514 is provided to each of the plurality of container holders 510. The plurality of holder support parts 520 support the plurality of container holders 510 such that each of the plurality of container holders 510 is movable in the x direction. The one or the plurality of guide rod 522 guides the plurality of holder support parts 520 in the x direction. The link mechanism 530 is connected to each of the plurality of holder support parts 520. The slide piece 540 is connected to the link mechanism 530 to cause the link mechanism 530 to slide between the smaller pitch and the larger pitch. The drive belt 550 causes the slide piece 540 to slide. The drive belt motor 560 drives the drive belt 550. A slide piece drive mechanism includes the drive belt 550 and the drive belt motor 560. The control unit 600 controls the operation of the slide piece drive mechanism (the drive belt motor 560).

A nucleic acid container 512*a* (FIG. 2) is held in each nucleic acid container holding space 512, and houses a nucleic acid extracted from a specimen. A specimen container 514*a* (FIG. 2) is held in each specimen container holding space 514, and houses a specimen transferred by the second nozzle 310 from the specimen container storage unit 126 on the second stage 120. The plurality of specimen container holding spaces 514 are disposed at a position closer to the plurality of processing lanes 112 than the plurality of nucleic acid container holding spaces 512 in the y direction. In other words, the plurality of container holders 510 house the plurality of specimen containers 514*a* at a position closer to the plurality of processing lanes 112 than the plurality of nucleic acid containers 512*a* in the y direction.

[Operation of Specimen Processing Apparatus]

The operation of the specimen processing apparatus will be described. First, in a first step, the second nozzle unit 300 transfers a plurality of specimens from the second stage 120 to the first stage 110. In the first step, the control unit 600 moves the second nozzle unit 300 in the y direction from the state shown in FIG. 3 by driving the main moving mechanism 400, and then stops the movement of the second nozzle unit 300 when the plurality of second nozzles 310 reach a position above a plurality of second specimen containers in the specimen container storage unit 126. In the state in which the plurality of second nozzles 310 are at the position above the plurality of second specimen containers, the plurality of second nozzles 310 are moved downward (in the z direction) in order to suction a plurality of specimens into a plurality of dispensing tips, which are mounted on the plurality of second nozzles 310, from the plurality of specimen containers in the specimen container storage unit 126.

Figure 6:
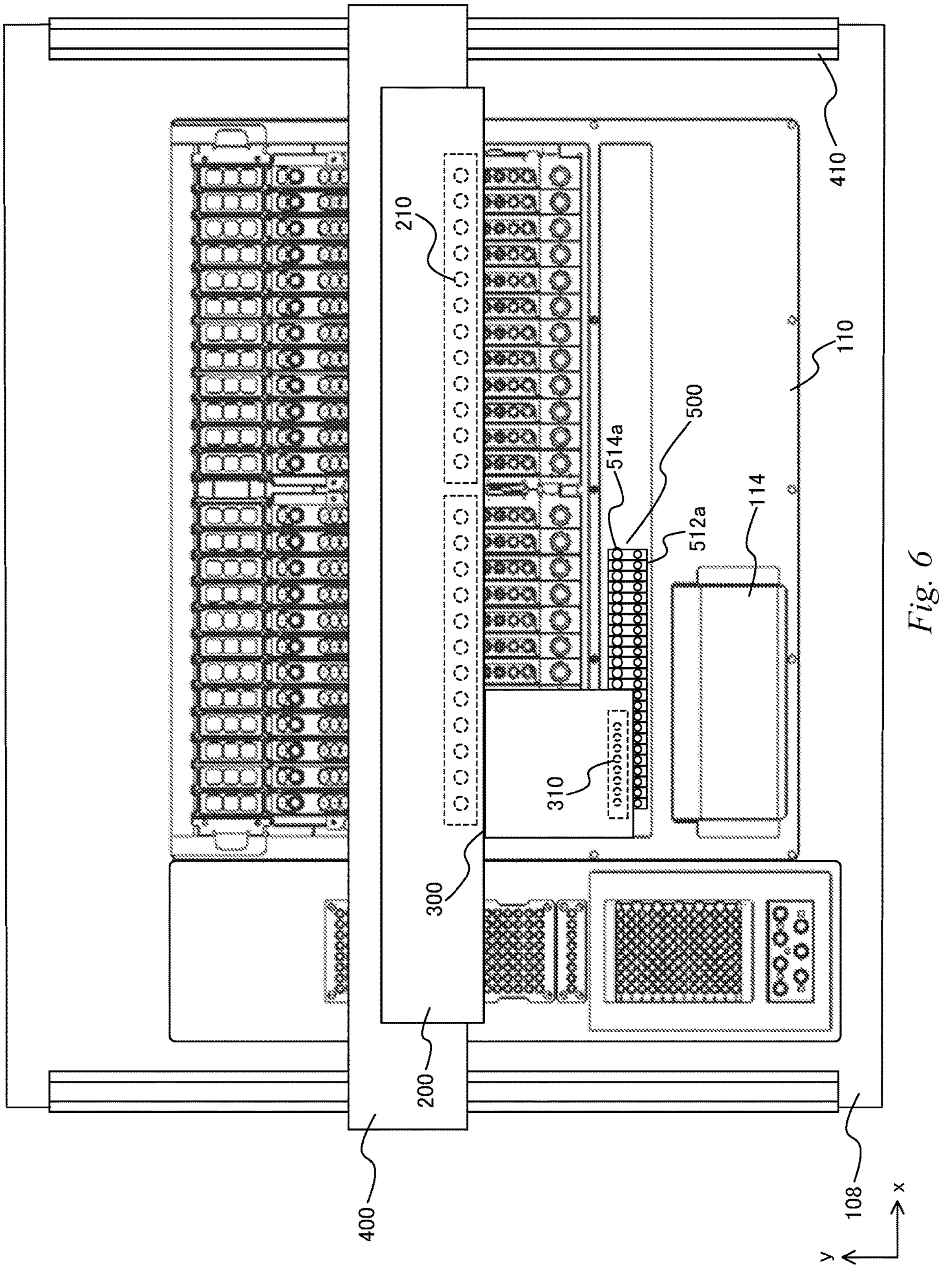
FIG. 6 is a top plan view showing an arrangement in which a second nozzle unit is at a position above the pitch conversion mechanism set to the smaller pitch.

Next, in the state in which the plurality of specimens are suctioned into the plurality of dispensing tips, the control unit 600 moves the second nozzle unit 300 to the state shown in FIG. 6. When the second nozzle unit 300 is in the state shown in FIG. 6, the plurality of second nozzles 310 are at a position above the plurality of specimen containers 514*a*. In the state shown in FIG. 6 in which the plurality of second nozzles 310 are at the position above the plurality of second specimen containers 514*a*, the plurality of second nozzles 310 are moved downward to discharge the plurality of specimens into the plurality of second specimen containers 514*a*.

Figure 7:
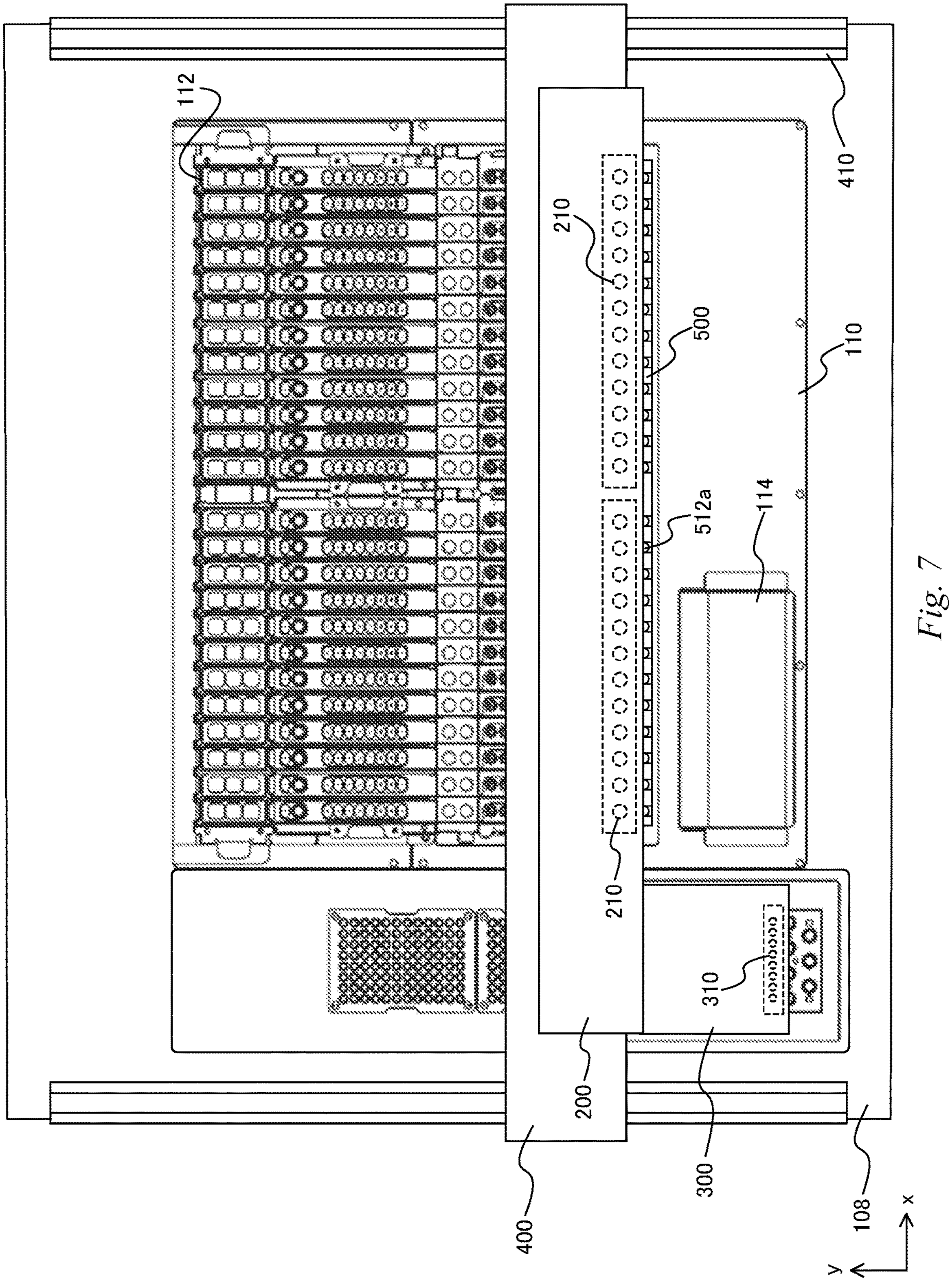
FIG. 7 is a top plan view showing an arrangement in which a first nozzle unit is at a position above the pitch conversion mechanism set to the larger pitch.

In a second step, the first nozzle unit 200 extracts nucleic acids from the plurality of specimens housed in the plurality of second specimen containers 514*a* on the first stage 110. After the plurality of specimens are transferred to the plurality of specimen containers 514*a* in the first step, in the second step, the first nozzle unit 200 and the second nozzle unit 300 are moved to the state shown in FIG. 2, and the pitch conversion mechanism 500 is moved to the larger pitch state shown in FIG. 2. Then, the first nozzle unit 200 is moved along the y direction to the position shown in FIG. 7. When the first nozzle unit 200 is in the position shown in FIG. 7, the pitch conversion mechanism 500 is set to the larger pitch, and the plurality of first nozzles 210 of the first nozzle unit 200 are at a position above the plurality of first specimen containers 514*a* of the pitch conversion mechanism 500. In the state in which the plurality of first nozzles 210 are at the position above the plurality of first specimen containers 514*a*, the plurality of first nozzles 210 are moved downward in order to suction the plurality of specimens in the plurality of first specimen containers 514*a* of the pitch conversion mechanism 500 into a plurality of dispensing tips mounted on the plurality of first nozzles 210.

The plurality of specimens are transferred to the plurality of processing lanes 112 in a state of being suctioned into the plurality of dispensing tips mounted on the plurality of first nozzles 210. The plurality of specimens transferred to the plurality of processing lanes 112 are subject to nucleic acid extraction processing by using the plurality of processing lanes 112 and the plurality of dispensing tips mounted on the plurality of first nozzles 210. Nucleic acid extraction is performed by a technique described in International Publication No. WO94/44671 filed by the inventors of the present invention, for example, that is, by using magnetic particles that bind to a target nucleic acid and a magnetic force mechanism (movable magnet) that adsorbs magnetic particles via a dispensing tip.

In a third step, the second nozzle unit 300 transfers the plurality of nucleic acids extracted on the first stage 110 to the PCR plate 128 on the second stage 120. First, after the extraction of nucleic acids on the plurality of processing lanes 112 is completed in the second step, the first nozzle unit 200 is moved to the position shown in FIG. 8 with the extracted nucleic acids held in the plurality of dispensing tips mounted on the plurality of first nozzles 210.

Figure 8:
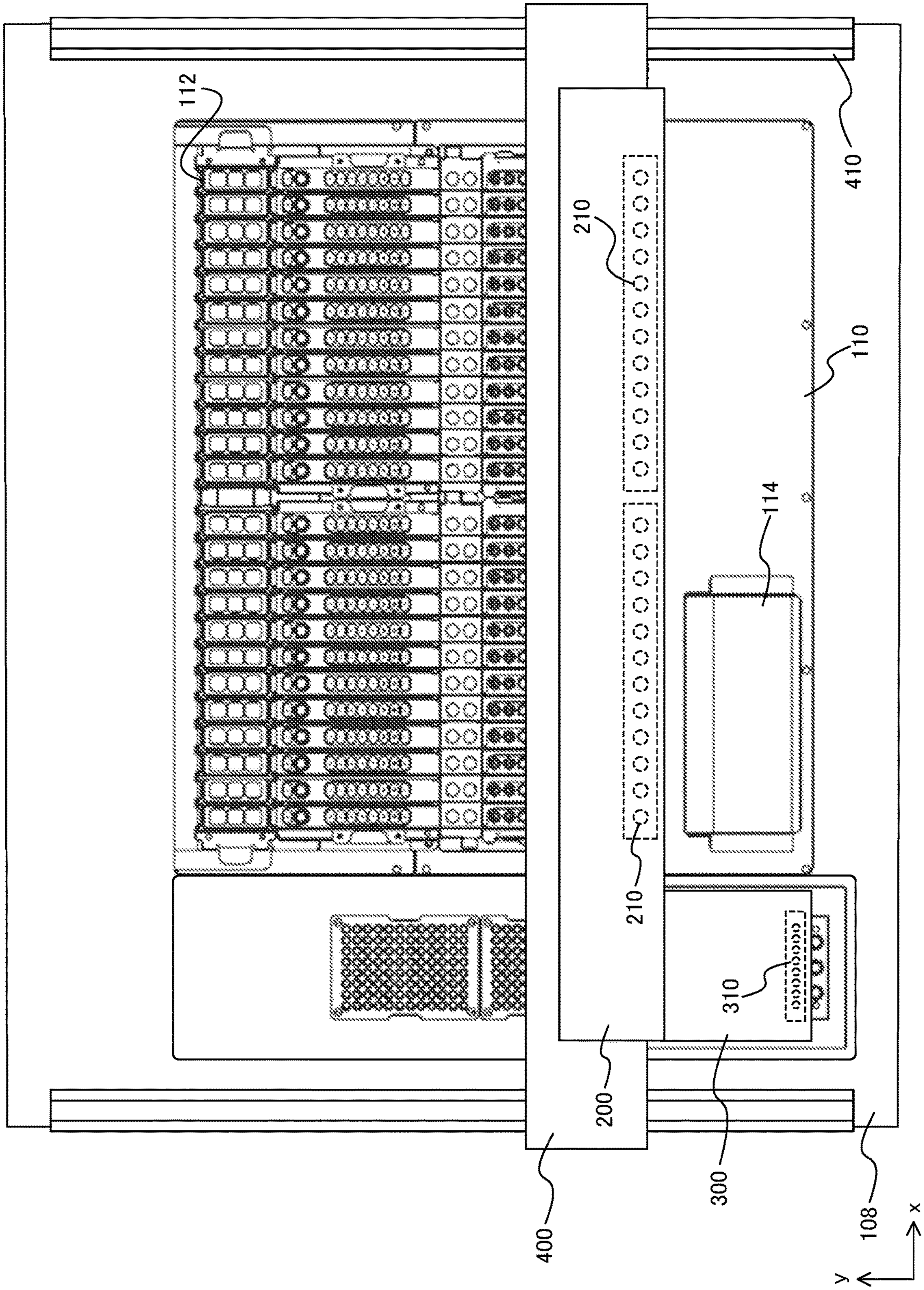
FIG. 8 is a top plan view showing an arrangement in which the first nozzle unit is at a position above the pitch conversion mechanism set to the larger pitch.
Figure 9:
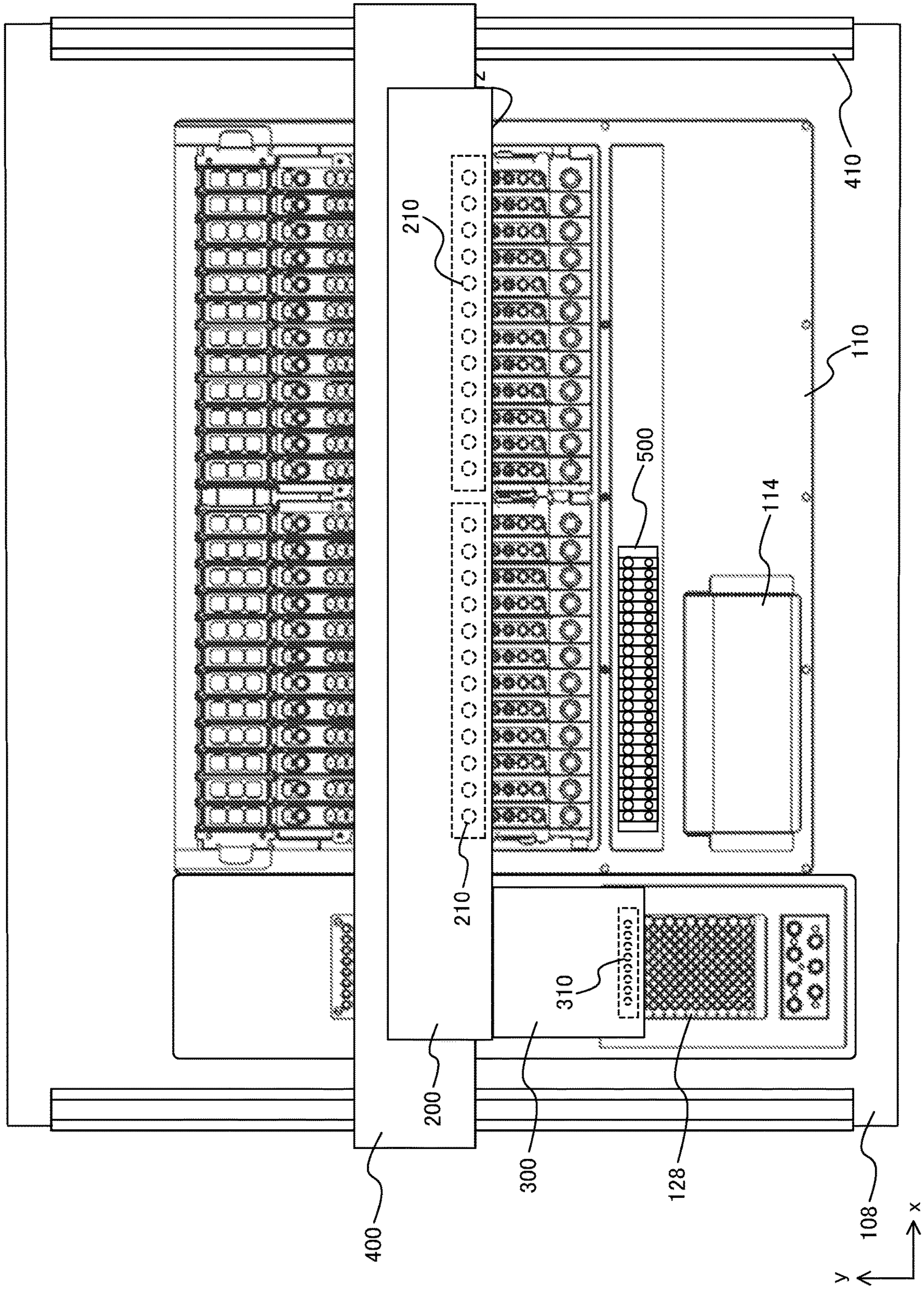
FIG. 9 is a top plan view showing an arrangement in which the second nozzle unit is at a position above a PCR plate.

When the first nozzle unit 200 is in the position shown in FIG. 8, the pitch conversion mechanism 500 is set to the larger pitch, and the plurality of first nozzles 210 of the first nozzle unit 200 are at the position above the plurality of first nucleic acid containers 512*a* of the pitch conversion mechanism 500. In the state in which the plurality of first nozzles 210 are at the position above the plurality of first nucleic acid containers 512*a*, the control unit 600 moves the plurality of first nozzles 210 downward in order to discharge a nucleic acid solution in the plurality of dispensing tips, mounted on the plurality of first nozzles 210, into the plurality of first nucleic acid containers 512*a* of the pitch conversion mechanism 500.

After the nucleic acid solution is discharged into the first nucleic acid containers 512*a*, the control unit 600 sets the pitch conversion mechanism 500 to the smaller pitch, and transfers the nucleic acid solution in the plurality of first nucleic acid containers 512*a* into a plurality of wells of the PCR plate 128 by using the plurality of second nozzles 310 of the second nozzle unit 300, the plurality of wells being arranged in one row along the x direction. After the second nozzle unit 300 transfers the nucleic acids to the PCR plate 128 in the third step, the operator moves the PCR plate 128 to a normal thermal cycler in order to perform PCR.

As a modification of the present embodiment, a pitch conversion mechanism moving mechanism may be provided that moves the pitch conversion mechanism 500 to the second stage 120 along the x direction.

REFERENCE SIGNS LIST

1000 specimen processing apparatus
100 base
200 first nozzle unit
210 first nozzle
300 second nozzle unit
310 second nozzle
400 main moving mechanism
500 pitch conversion mechanism
510 container holder
600 control unit

The invention claimed is:

1. A specimen processing apparatus extracting nucleic acids from each of a plurality of specimens, the specimen processing apparatus comprising:

a plurality of container holders configured to hold a plurality of first specimen containers and/or a plurality of first nucleic acid containers in one row along a first direction, the plurality of first specimen containers housing the plurality of specimens along the first direction, the plurality of first nucleic acid containers housing the nucleic acids extracted along the first direction;

a pitch conversion mechanism configured to convert a pitch of the plurality of container holders along the first direction between a smaller pitch and a larger pitch;

a plurality of processing lanes extending in a second direction in parallel in order to concurrently extract the nucleic acids from the plurality of specimens;

a first nozzle unit including a plurality of first nozzles arranged in one row along the first direction at the larger pitch, the first nozzle unit being configured to move over the plurality of processing lanes along the second direction;

a second container housing unit configured to house a plurality of second specimen containers and/or a plurality of second nucleic acid containers, the plurality of second specimen containers being arranged in one row along the first direction at the smaller pitch, the plurality of second nucleic acid containers being arranged in one row along the first direction at the smaller pitch;

a second nozzle unit including a plurality of second nozzles arranged in one row along the first direction at the smaller pitch, the second nozzle unit being configured to move between a region above the plurality of container holders set to the smaller pitch and a region above the second container housing unit; and a control unit configured to control an operation of the pitch conversion mechanism, an operation of the first nozzle unit, and an operation of the second nozzle unit.

2. The specimen processing apparatus according to claim 1, comprising a main moving mechanism configured to move the first nozzle unit in the second direction.

3. The specimen processing apparatus according to claim 2, wherein the main moving mechanism moves the second nozzle unit in the second direction.

4. The specimen processing apparatus according to claim 2, wherein the main moving mechanism moves the first nozzle unit and the second nozzle unit as an integral body.

5. The specimen processing apparatus according to claim 1, comprising a sub-moving mechanism configured to move the second nozzle unit in the first direction.

6. The specimen processing apparatus according to claim 1, wherein the second container housing unit that houses the plurality of second nucleic acid containers is a PCR plate having a plurality of wells.

7. The specimen processing apparatus according to claim 1, comprising a pitch conversion mechanism moving mechanism configured to move the pitch conversion mechanism in the first direction.

8. The specimen processing apparatus according to claim 1, wherein the plurality of container holders, the pitch conversion mechanism, and the plurality of processing lanes are disposed on a first stage.

9. The specimen processing apparatus according to claim 8, wherein the first nozzle unit moves over the first stage.

10. The specimen processing apparatus according to claim 8, wherein the first stage is provided with a dispensing tip disposal unit configured to dispose of dispensing tips mounted on the plurality of first nozzles and/or dispensing tips mounted on the plurality of second nozzles.

11. The specimen processing apparatus according to claim 1, wherein the second container housing unit is disposed on a second stage.

12. The specimen processing apparatus according to claim 11, comprising a cooling mechanism configured to cool the second container housing unit.

13. The specimen processing apparatus according to claim 11, wherein the second nozzle unit moves over at least the second stage.

14. The specimen processing apparatus according to claim 1, wherein the plurality of container holders house the plurality of specimen containers at a position closer to the plurality of processing lanes than the plurality of nucleic acid containers in the second direction.

15. The specimen processing apparatus according to claim 1, wherein the pitch conversion mechanism includes a plurality of holder support parts, a link mechanism, a slide piece, and a slide piece drive mechanism, the plurality of holder support parts being configured to support the plurality of container holders such that each of the plurality of container holders is movable in the first direction, the link mechanism being connected to the plurality of holder support parts, the slide piece being configured to cause the link mechanism to slide between the smaller pitch and the larger pitch, the slide piece drive mechanism being configured to drive the slide piece.

* * * * *